United States Patent
Zhang et al.

(10) Patent No.: US 9,273,238 B2
(45) Date of Patent: Mar. 1, 2016

(54) PROCESS FOR FUNGAL MODIFICATION OF LIGNIN AND PREPARING WOOD ADHESIVES WITH THE MODIFIED LIGNIN AND WOOD COMPOSITES MADE FROM SUCH ADHESIVES

(76) Inventors: Yaolin Zhang, Quebec (CA); Dian-Qing Yang, Quebec (CA); Xiang-Ming Wang, Quebec (CA); Martin Feng, Vancouver (CA); Gilles Brunette, Quebec (CA)

(*) Notice: Subject to any disclaimer, the term of this patent is extended or adjusted under 35 U.S.C. 154(b) by 0 days.

(21) Appl. No.: 14/001,089

(22) PCT Filed: Feb. 17, 2012

(86) PCT No.: PCT/CA2012/000153
§ 371 (c)(1),
(2), (4) Date: Nov. 5, 2013

(87) PCT Pub. No.: WO2012/113058
PCT Pub. Date: Aug. 30, 2012

(65) Prior Publication Data
US 2014/0163142 A1    Jun. 12, 2014

Related U.S. Application Data

(60) Provisional application No. 61/445,725, filed on Feb. 23, 2011.

(51) Int. Cl.
*C09J 161/06*    (2006.01)
*C08G 8/20*    (2006.01)
(Continued)

(52) U.S. Cl.
CPC ............ *C09J 161/06* (2013.01); *C08G 8/20* (2013.01); *C08G 8/24* (2013.01); *C08H 6/00* (2013.01);
(Continued)

(58) Field of Classification Search
CPC ........ C08L 61/06; C08L 97/02; C09J 161/06; C09J 197/02; C12P 7/22

USPC .............. 524/14; 435/156, 254.1; 527/400; 530/500, 501
See application file for complete search history.

(56) References Cited

U.S. PATENT DOCUMENTS 2,671,751 A * 3/1954 Jennison et al. ............. 435/277
2,698,307 A * 12/1954 Heritage ..................... 524/13
(Continued)

OTHER PUBLICATIONS

Job, D., "Assessment of selected decay Basidiomycetes for selective biodefibrillation of Picea abies wood," Mycological Progress, 2002, 1, 123-129.*

(Continued)

*Primary Examiner* — Liam J Heincer
*Assistant Examiner* — Nicholas Hill
(74) *Attorney, Agent, or Firm* — Norton Rose Fulbright Canada LLP (57) ABSTRACT

Disclosed herein are method to modify the lignin with particular fungal species, and procedure to synthesize phenolic adhesives with the modified lignin as raw materials, and the adhesives compositions and methods for making adhesive compositions, and methods for making lingo-cellulosic composites from renewable materials. Four fungi in examples are *Lenzites elegans* (Spreng.) Pat. (FTK 329A), *Phanerochaete cremea* (Bres.) Parmasto (FTK 332A), *Pycnoporellus alboluteus* (Ellis & Everh.) Kotl. & Pouz. (FTK 76A) and *Meruliopsis taxicola* (Pers.) Bondartsev (FTK 122B). Lignin used in examples are organosolv lignin, Kraft lignin, and ammonium lignosulfonate. The present invention includes methods to (1) modify of lignin with fungi; (2) in-situ polymerize modified lignin-phenol-formaldehyde to generate bio-modified lignin-phenol-formaldehyde adhesive in liquid form, and (3) manufacture composite panels with bio-modified lignin-phenol-formaldehyde resins.

8 Claims, 1 Drawing Sheet

$\lambda_{max} = 280$ nm     $\lambda_{max} = 250, 300$ and $350\text{-}400$ nm Scheme of phenolic hydroxyl group at alkali condition (51) Int. Cl.
    *C08G 8/24*     (2006.01)
    *C09J 161/12*     (2006.01)
    *C12N 1/14*     (2006.01)
    *C12R 1/645*     (2006.01)
    *C12P 1/02*     (2006.01)
    *C08H 7/00*     (2011.01)
    *C08L 97/00*     (2006.01)
    *C09J 197/02*     (2006.01)
    *C12P 7/22*     (2006.01)

(52) U.S. Cl.
    CPC ............ *C08L 97/005* (2013.01); *C09J 161/12* (2013.01); *C09J 197/02* (2013.01); *C12N 1/14* (2013.01); *C12P 1/02* (2013.01); *C12P 7/22* (2013.01); *C12R 1/645* (2013.01)

(56) References Cited

U.S. PATENT DOCUMENTS

| | | | | |
|---|---|---|---|---|
| 3,962,033 | A * | 6/1976 | Eriksson | D21C 5/005 162/72 |
| 4,432,921 | A * | 2/1984 | Haars et al. | 264/109 |
| 5,010,156 | A * | 4/1991 | Cook et al. | 527/403 |
| 6,555,649 | B2 * | 4/2003 | Giroux et al. | 530/200 |
| 2004/0220368 | A1* | 11/2004 | Li et al. | 527/400 |

OTHER PUBLICATIONS

Lara, M. A., et al., "Black liquor lignin biodegradation by Trametes elegans," International Biodeterioration & Biodegradation, 2003, 52, 167-173.*

Species Fungorum website, GSD Species Synonymy for "Lenzites elegans", downloaded on Sep. 25, 2014.*

Species Fungorum website, GSD Species Synonymy for "Gloeoporus taxicola", downloaded on Sep. 25, 2014.*

Mycobank, entry for Peniophora cremea, at www.mycobank.org, downloaded Sep. 4, 2015.*

Hüttermann, A., O. Milstein, B. Nicklas, J. Trojanowski, A. Haars, A. Kharazipour, Lignin: Chapter 27: Enzymatic Modification of Lignin for Technical Use: Strategies and Results, ACS Symposium Series, vol. 397, pp. 361-370 (1989).

Jin L, T. Sellers. Jr. T. P. Schultz and D. D. Nicholas, Utilization of lignin modified by brown-rot fungi: I. Properties of Flakeboard Produced with a Brown-rotted Lignin Modified Phneolic Adhesive, Holzforchung, 44, 207-210 (1990).

Li, K C, From Mussels to decayed wood: an evolving story of developing green wood adhesives from renewable natural resources, 39th International Wood Composites Symposium, Apr. 4-7, 2005, Pullman, Washington, USA.

Sellers, T. Jr., Wood adhesive innovations and applications in North America, Forest Products Journal, 51, 12-22 (2001).

Zakis. G. F. Functional analysis of lignins and their derivatives. Tappi Press, 48-49 (1994).

International Search Report for PCT/CA2012/000153.

* cited by examiner

Figure 1

Scheme of phenolic hydroxyl group at alkali condition

Figure 2

Formula of four different phenolic hydroxyl groups

PROCESS FOR FUNGAL MODIFICATION OF LIGNIN AND PREPARING WOOD ADHESIVES WITH THE MODIFIED LIGNIN AND WOOD COMPOSITES MADE FROM SUCH ADHESIVES

CROSS-REFERENCE TO RELATED APPLICATIONS

This application is a National entry of PCT/CA2012/000153 filed Feb. 17, 2012, in which the United States of America was designated and elected, and which remains pending in the international phase until Aug. 23, 2013, which application in turn clams priority under 35 USC 119(e) from U.S. Provisional Application Ser. No, 61/445,725, filed Feb. 23, 2011.

FIELD OF THE INVENTION

The present invention relates to adhesives made with fungal-modified lignin and the wood composites that are made from the adhesives.

BACKGROUND

The shortage of high-quality standing lumber has driven researchers and wood products manufacturers to look for alternative low-quality resources for value-added applications. To achieve these goals, suitable technologies are needed to improve specific wood quality attributes (e.g., dimensional stability, durability, mechanical properties, and hardness) in order to meet end-use requirements. Low-quality resources can be modified through different treatments to acquire the attributes necessary to meet specific requirements. Lignocellulosic composite materials have been used in many structural applications as substitutes for traditional lumber. These lignocellulosic composites are made from lignocellulosic materials comprised of wood strands, wood fibers or wood chips, and the wood adhesives (less than 10% based oven dry cellulosic material), and are formed at elevated temperatures and pressures.

Wood adhesives are key components for wood composites. Sellers (2001) reported that North American consumed more than $1.78 \times 10^8$ tons of wood adhesives (solid basis) in 1998, in which urea-formaldehyde (UF) and melamine-formaldehyde (MF) adhesives account for around 60%, and phenol-formaldehyde (PF) adhesive accounts for over 30%. Because of formaldehyde release during the usage of wood composites with UF or MF or melamine-urea-formaldehyde (MUF) adhesives, these adhesives are facing challenges from current and near future regulations. Because of the thermal resistance and weather resistance compared to other wood adhesives such as UF resin, MF resin and isocyanate adhesives, PF resins are commonly used for weather proof particleboard, OSB, MDF and/or plywood for use under exterior weather conditions. Apart from that, PF resin usually has very low formaldehyde emission in service.

PF resin is produced from petroleum products. Petroleum reserves are naturally limited. Thus the wood composites industry would benefit greatly from the development of green lignin-based phenolic resin.

The wood-decomposing fungi can be divided into two groups according to their modes of action on wood materials: brown-rot and white-rot fungi. Brown-rot fungi can degrade wood polysaccharides and leave behind a brown, partially modified (oxidized) lignin residue. Some brown-rot fungi can also produce laccase in liquid culture, but the laccases produced by brown-rot fungi have a low redox potential that allows direct oxidation only of phenolic lignin units, which often comprises less than 10% of the total polymer. White-rot fungi can degrade both polysaccharides and lignin selectively or simultaneously and leave a cellulose-enriched white material. They often invade the lumens of wood cells and cause progressive lignin degradation between fibres.

Hüttermann et al (1989) reviewed the enzymatic modification of lignin for technical use to produce a homogeneous, pure lignin preparation of reasonably high molecular weight with high reactivity provided by reactive functional groups. Ligninase, laccase, and poly-blue-oxidase three enzymes that change the lignin structure through different mechanisms. Ligninase is the main lignolytic system in white-rot fungi, and can catalyze the oxidation of veratryl alcohol. Laccase acts on phenolics via a non-specific oxidation. Presence of laccase showed polymerization of ligninase both in vivo and in vitro. The low molecular weight substances from enzymatically degraded lignin are rarely re-polymerized. Poly-blue-oxidase oxidizes the lignin model compound poly-blue.

Lignin is a recalcitrant molecule that does not lend itself to adhesive manufacture without modification. One way of doing this is using wood-decomposing fungi (Jin et al 1990).

Li (2005) made a presentation about developing green wood adhesives from renewable natural resources. He mentioned that brown-rot fungi preferentially degrade carbohydrates, but do not substantially depolymerise lignin. The brown-rot fungi demethylate lignin and oxidize lignin side chains to some extent. He used natural brown-rot fungi-decayed Douglas-fir wood from the forest dissolved in a dilute sodium hydroxide solution and the soluble decayed wood was reduced with sodium hydroxide, and mixed with polyethyleneimine used for wood adhesives.

Jin et al (1990) extracted extensively brown-rotted Douglas-fir wood by refluxing with 0.1N sodium hydroxide, acidified the solution with 0.1N hydrochloric acid to precipitate lignin (BRL) (pH 3-4), then centrifuged, washed and freeze-dried it. The phenol-formaldehyde resin with 35% wt BRL substitution of phenol was formulated.

SUMMARY OF THE INVENTION

Disclosed herein are 1) a method to modify the lignin with particular fungal species, 2) a procedure to synthesize phenolic adhesives with the modified lignin as raw materials, 3) the adhesives compositions and methods for making adhesive compositions, and 4) methods for making lignocellulosic composites from renewable materials.

A first variant of an adhesive composition described herein, liquid form at least one lignin component, at least phenol component, and at least formaldehyde component reacted at elevated temperatures and a certain period of time. In this invention, both brown-rot and white-rot fungi were used for lignin modification in resin manufacturing.

In accordance with one aspect of the present invention, there is provided a process for the preparation of polymer adhesives comprising the steps of: providing a fungal species selected from the group consisting of *Lenzites elegans, Phanerochaete cremea, Pycnoporellus alboluteus* and *Meruliopsis taxicola* and combinations thereof; providing a lignin; preparing each of the fungal species; preparing the lignin for fungal species modification of the lignin; mixing the prepared fungal species and the prepared lignin to produce a lignin/fungal species suspension; incubating the suspension; separating the suspension into a solid comprising the fungal species and a liquid comprising the modified lignin; and treating the liquid to produce a reactive solid for the polymer adhesive.

In accordance with another aspect of the process described herein, further comprising: providing at least one phenolic compound, at least one formaldehyde compound, an alkali metal hydroxide and water; mixing the at least one phenolic compound, the at least one formaldehyde compound, the alkali metal hydroxide, the water and the reactive solid to produce a methylolation medium (at a pH of about 10 or less); maintaining the medium at a methylolation temperature to produce a methylolated medium reacting with the water predominantly; and increasing the temperature of the methylolated medium to produce the phenol-formaldehyde polymer via a condensation reaction.

In accordance with yet another aspect of the process described herein, further comprising adding more of the alkali metal hydroxide to the methylolated medium.

In accordance with still another aspect of the present invention, there is provided a lignin modifying fungus comprising: a fungal species selected from the group consisting of *Lenzites elegans, Phanerochaete cremea, Pycnoporellus alboluteus* and *Meruliopsis taxicola* and combinations thereof; cultured in aqueous malt extract broth and pH adjusted for lignin modification wherein the pH is adjusted between 5 and 6.

In accordance with yet still another aspect of the fungus described herein, the fungus is further cultured for 14 days at 25° C.

In accordance with yet a further aspect of the present invention, there is provided a phenol formaldehyde adhesive polymer comprising: a phenolic compound selected from the group consisting of phenol, a lignin or combinations thereof; a formaldehyde compound selected from the group consisting of formaldehyde, paraformaldehyde and combinations thereof; water; and an alkali metal hydroxide; wherein the lignin is a *Lenzites elegans, Phanerochaete cremea, Pycnoporellus alboluteus, Meruliopsis taxicola* and combinations thereof modified lignin, wherein the weight percentage of the modified lignin is at least 33% of the phenolic compound.

In accordance with still a further aspect of the polymer described herein, wherein the weight percentage of the modified lignin is at least 50% of the phenolic compound.

In accordance with yet still a further aspect of the present invention, there is provided a plywood comprising phenol formaldehyde adhesive polymer between wooden layers of the plywood; wherein the adhesive polymer comprising: a phenolic compound selected from the group consisting of phenol, a lignin or combinations thereof; a formaldehyde compound selected from the group consisting of formaldehyde, paraformaldehyde and combinations thereof; water; and an alkali metal hydroxide; wherein the lignin is a *Lenzites elegans. Phanerochaete cremea, Pycnoporellus alboluteus, Meruliopsis taxicola* and combinations thereof modified lignin, wherein the weight percentage of the modified lignin is at least 33% of the phenolic compound.

In accordance with one embodiment of the plywood described herein, the weight percentage of the modified lignin is at least 50% of the phenolic compound.

Also disclosed herein are preparation examples of lignocellulosic composites comprising the lignocellulosic materials and adhesive compositions, methods for making such adhesives, and methods for making the composites.

The process according to the invention consists in 1) modifying the lignin with particular fungal species; 2) synthesizing a resin based on the modified lignin; and 3) manufacturing wood composites with the adhesives and evaluating their performance.

DETAILED DESCRIPTION OF THE INVENTION

For better understanding, the terms used herein are described below in more details:

"Lignin" generally refers to a group of phenolic polymers that give strength and rigidity to plant materials. Lignins are complex polymers, and tend to be referred to in generic terms. Lignins may include, for example, industrial lignin preparations, such as Kraft lignin, lignosulfonates, organosolv lignin from by-products of bio-ethanol process, and analytical lignin preparation, such as dioxane acidolysis lignin, milled wood lignin. Klason lignin, cellulolytic enzyme lignin, etc.

"Lignin component" represents any lignin-containing material. Lignin component can be derived from industrial lignin preparation, analytical lignin preparation, and etc, which are from renewable resources, especially from lignocelluloses. The lignin component can be a material or a composition, which is a modified, treated or purified portion of lignin.

"Lignocellulosic materials" include all plant materials. For example, materials include wood materials (such as wood strands, wood fibers, wood chips or wood particles), grass materials (such as hemp or flax), grain materials (such as the straw of rice, wheat, corn), etc.

The above term descriptions are provided only to aid the reader, should not be constructed to have a scope as limiting the scope of the appended claims.

Phenol-formaldehyde (PF) resins are usually prepared from two main chemicals that are reacted at elevated temperatures through methylolation and condensation to form a phenolic polymer. The polymer formation is strongly related to the molar ratio of phenol to formaldehyde, and the pH at which the reaction takes place. The phenolic resin is known as a "Novolac" resin when the molar ratio of formaldehyde to phenol is less than 1 and its pH is low (acidic conditions). On the contrary, the phenolic resin will be of "Resol" type if the molar ratio of formaldehyde to phenol is higher than 1, and its pH is higher than 7 (alkali conditions). Resol type phenolic resins will crosslink, usually at elevated temperatures.

The basic purpose of the present invention is to modify lignin with fungi, increasing its reactivity towards formaldehyde, and then to incorporate a large amount of it into phenol-formaldehyde adhesive system to form a copolymer (lignin-formaldehyde, lignin-formaldehyde-phenol), to lower the cost and improve the bonding and mechanical properties of wood composites.

More specifically, the four purposes of the present invention are:

1) To modify the lignin with bio-technology to obtain more reactive technical lignin;

2) To incorporate a large amount of lignin into phenolic resin through in-situ polymerization;

3) To provide a process for preparing thermoset adhesives wherein a lignin is used in significant amounts to copolymerize with phenol and formaldehyde;

4) To make wood composites with the resulting phenolic resins.

As aforementioned, the amount of phenol that can be substituted in the formulation can be up to 50% by weight of lignin (the preferred range being 30%, 33% or higher by weight) and the resulting adhesives still meet the CSA and ASTM standard requirements for bond strength in oriented strand board (OSB) and/or plywood.

The use of lignin reduces the amount of phenol and formaldehyde solids required to form the resin. In this connection, the lignin is to react with formaldehyde with methylation reaction and then to form a copolymer through condensation reaction. The product obtained by the present invention is a lignin-phenol-formaldehyde copolymer adhesive.

The first stage of the process according to the invention is to modify lignin with bio-technology, which involves several sub-steps as follows:

1) Providing the fungal species: four fungal species were selected from 45 fungi tested to modify lignin, based on their growth rates and discoloration speed on a Poly R-478 enriched medium. Poly R-478 is a homogeneous reagent that is easy to be used for an exact determination of the degree of lignin degradation. These fungi were *Lenzites elegans* (Spreng.) Pat. (FTK 329A), *Phanerochaete cremea* (Bres.) Parmasto (FTK 332A), *Pycnoporellus alboluteus* (Ellis & Everh.) Kotl. & Pouz. (FTK 76A) and *Meruliopsis taxicola* (Pers.) Bondartsev (FTK 122B). The first two species, *L. elegans* and *P. cremea*, represent white-rot fungi and were characterized by producing enzymes that strongly react with gallic acid and tannic acid in a medium. The later two species, *P. alboluteus* and *M. taxicola*, representing brown-rot fungi were characterized by a negative reaction on the gallic acid and tannic acid medium. All these fungal species came from the Culture Collection of Wood-inhabiting Fungi (FTK series) of FPInnovations, Québec, Canada. The fungal cultures were maintained in a liquid nitrogen reservoir for cryopreservation at −198° C. before use.

2) Preparing the fungal species for lignin modification: the selected fungal species were retrieved from the liquid nitrogen reservoir and grown on a 2% (w/w) malt extract agar medium in Petri plates at 25° C. for one week. Mycelia plugs (5 mm in diameter) were cut from each fungal colony and transferred to 1-L flasks (5 plugs in each) containing 450 ml of a 2% (w/w) Difco malt extract broth (Becton, Dickinson and Company, Sparks, Md., USA) in distilled water. The pH of the medium was 5.5. The flasks were cultured on a shaker (125 rpm) at 25° C. for 14 days.

3) Preparing a lignin for fungal modification: the lignin to be modified was first sterilized in an oven with heat at 70° C. for 2 hours.

3) i) After cooling, 50 g of lignin were weighed and around 20% suspensions were made with sterile distilled water, or other suitable solvents.

3) ii) The pH of lignin was adjusted to around 5.5-6.0 with inorganic acid (such as sulphuric acid, hydrochloric acid, etc.) if the pH of the suspension was higher than 8, or with alkali chemicals (such as potassium hydroxide, sodium hydroxide, etc.) if the pH of the suspension was lower than 4.

4) Mixing/incubation of lignin with the prepared fungal species: lignin suspensions were added to each flask that contained 14-day old fungal cultures under sterile conditions. The concentration of lignin in fungal culturing flasks was approximately 10% (w/w).

4) i) The flasks were put back on the shaker (125 rpm) for a further culturing period of 21 days at 25° C.

5) Separating the incubated suspension: after incubation, the suspension including the fungal cultures and fungal modified lignin in the flasks, were filtered through a layer of cotton cloth. The fungal mycelia filtered on the top of the cotton cloth was discarded, and fungal modified lignin in the liquid phase was collected.

5) i) The collected fungal modified lignin in liquid was poured in a shallow dish and dried in an oven at 50° C. for 48 hours to dryness. The fungal modified lignin powder was collected from the dish and used for resin synthesis.

The second stage of the process according to the invention is to synthesize bio-modified-lignin based phenolic resin. The sub-steps are as follows:

1) Mixing lignin with phenol, formaldehyde, alkali chemical, and water, and letting the obtained mixture react at elevated temperatures.

2) The order of addition of the above starting compounds is not critical, but it is preferred to load phenol, then lignin, after that, formaldehyde (37% wt), and water, then raise temperature to 50-60° C. When desired temperature is reached, load sodium hydroxide in the form of a solution containing 50% by weight of sodium hydroxide. The prepared mixture is heated to a temperature of 60-75° C., preferably ~70° C., for a period of 1 to 2 hours. The methylolation reaction takes place in which formaldehyde reacts on the ortho-position of the phenol and with available sites on the lignin.

3) Loading more 50% by weight sodium hydroxide solution and water in the system, while maintaining the temperature at 60-75° C. The period of time is, for example, 10 minutes to 1 hour. The methylolation reaction continues. Such a two-steps processing is actually important. Indeed, the same process could be made in only one stage, but doing such may not produce the same resin. Furthermore, a resin obtained in a one-step reaction may not have the same quality as the resin produced in two steps.

4) Raising the temperature to 75-95° C. (preferably in the 80-85° C. range) so the condensation reaction of methylolated lignin with methylolated phenol occurs, for a certain period of time. At this stage, control of the temperature is important. Otherwise proper viscosity may not be achieved. The viscosity varies for different applications, i.e. around 100-200 cP (centipoise) for OSB resins with a solid content of ~45% by weight, around 250-300 cP or over for plywood making, and around 60-200 cP for powder resin applications.

The amounts of raw materials added at each stage, the temperature at which the addition is carried out and/or the molar ratios of formaldehyde to phenol may vary depending on the needs. In practice, the molar ratio of formaldehyde to phenol preferably ranges from 1.8:1 to 3.0:1. More preferably, the molar ratio will range from 2.2:1 to 2.8:1 to achieve better results. The weight ratio of phenol (and lignin if applicable) to base (sodium hydroxide or potassium hydroxide) ranges from 0.03 to 0.30. More preferably, the weight ratio ranges from 0.08 to 0.15 to achieve better results.

EXAMPLE 1

Modification of Organosolv Lignin with Fungus *Pycnoporellus alboluteus* (FTK 76A)

Fungus *Pycnoporellus alboluteus* (Ellis & Everh.) Kotl. & Pouz. (FTK 76A) [a brown-rot fungus, from the Culture Collection of Wood-inhabiting Fungi (FTK series) of FPInnovations, Quebec, Canada, maintained in a liquid nitrogen reservoir for cryopreservation at −198° C. before use] and organosolv lignin were used.

The selected fungal species FTK 76A was retrieved from the liquid nitrogen reservoir and grown on a 2% (w/w) malt extract agar medium in Petri plates at 25° C. for one week. Mycelia plugs (5 mm in diameter) were cut from each fungal colony and transferred in 1-L flasks (5 plugs in each) containing 450 mL of a 2% (w/w) Difco malt extract broth (Becton, Dickinson and Company, Sparks, Md. USA) in distilled water. The pH of the medium was 5.5. The flasks were cultured on a shaker (125 rpm) at 25° C. for 14 days.

The organosolv lignin was first sterilized in an oven at 70° C. for 2 hours. After cooling, 50 g of lignin was weighed in each flask that contained 14-day old fungal cultures under sterile conditions. The concentration of lignin in fungal culturing flasks was approximately 10% (w/w). The flasks were put back on the shaker (125 rpm) for a further culturing period of 21 days at 25=C. After incubation, the fungal cultures and lignin in the flasks were filtered through a layer of cotton cloth. The fungal mycelia filtered on the top of the cotton cloth were discarded, and lignin in the liquid phase was collected. The collected lignin in liquid was poured in a shallow dish and dried in an oven at 50° C. for 48 hours to dryness. The fungal modified lignin powder was collected from the dish, which is coded OLEA.

EXAMPLES 2-4

Modification of Organosolv Lignin with Different Fungi

The procedure and conditions were the same as EXAMPLE 1. The only difference was fungal species. The example numbers and fungal species are listed in Table 1.

TABLE 1

Modification of organosolv lignin with different fungi

| EXAMPLE | Fungal specie | Type of fungi | Lignin | Code |
|---|---|---|---|---|
| 1 | *Pycnoporellus alboluteus* (Ellis & Everh.) Kotl. & Pouz. (FTK 76A) | brown-rot | organosolv lignin | OLEA |
| 2 | *Phanerochaete cremea* (Bres.) Parmasto (FTK 332A) | white-rot | | OLEB |
| 3 | *Lenzites elegans* (Spreng.) Pat. (FTK 329A) | white-rot | | OLEC |
| 4 | *Meruliopsis taxicola* (Pers.) Bondartsev (FTK 122B) | brown-rot | | OLED |

Figure 1:
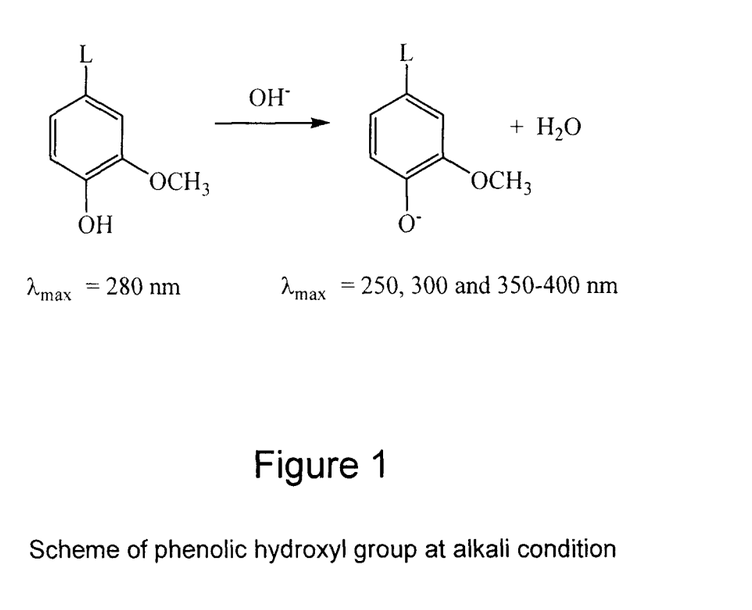
FIG. 1 illustrates the method for quantifying phenolic hydroxyl groups and α-conjugated phenolics based on absorbance.
Figure 2:
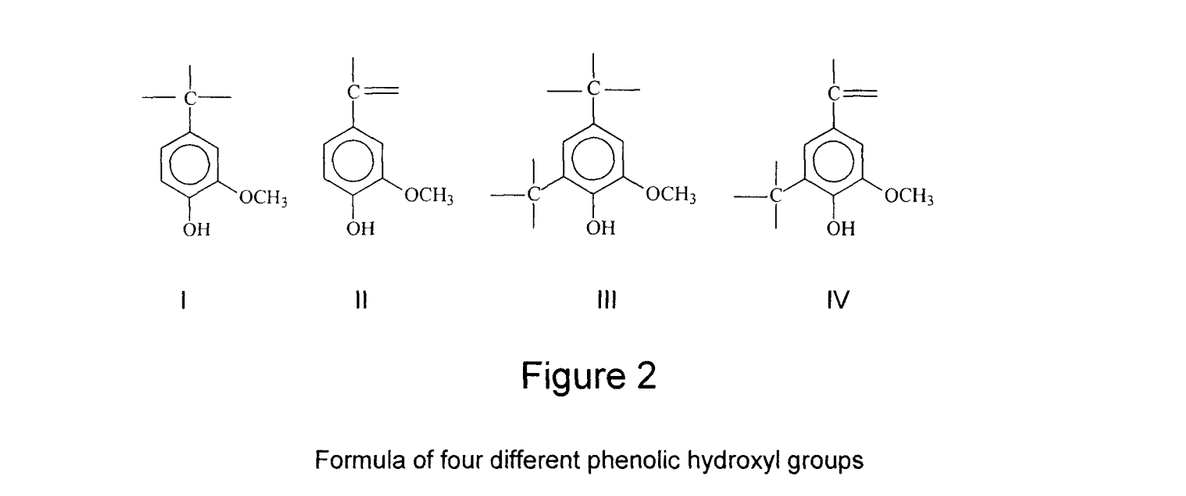
FIG. 2 illustrates four different phenolic groups that were quantified by the method illustrated in FIG. 1.

Ultraviolet-spectroscopy offers a simple and rapid way of determining phenolic hydroxyl groups (Zakis, 1994). Phenolic hydroxyl group and proportion of α-conjugated phenolics were calculated based on the absorbance values at 300 nm and 350 nm-365 nm with difference buffer solution at pH6, pH12, and with 0.2N NaOH as shown in FIGS. 1 and 2 (Zakis, 1994). The method of quantifying phenolic hydroxyl groups and α-conjugated phenolics is based on the following:

FIG. 1

Table 2 shows that the types of phenolic hydroxyl groups and quantity of phenolic hydroxyl groups that were modified.

TABLE 2

Phenolic hydroxyl group of unmodified and bio-modified organosolv lignin

| | Unmodified lignin | OLEA | | OLEB | | OLEC | | OLED | |
|---|---|---|---|---|---|---|---|---|---|
| | | Value | Changes, % | Value | Changes, % | Value | Changes, % | Value | Changes, % |
| Total phenolic hydroxyl group, % | 2.052 | 1.597 | −22.77 | 1.628 | −20.66 | 2.711 | 32.12 | 2.412 | 17.54 |
| I, %  | 0.717 | 0.736 | 2.65 | 1.102 | 53.70 | 0.961 | 34.03 | 1.194 | 66.53 |
| II, %  | 0.180 | 0.160 | 11.11 | 0.208 | 15.56 | 0.196 | 8.89 | 0.254 | 41.11 |

TABLE 2-continued

Phenolic hydroxyl group of unmodified and bio-modified organosolv lignin

| | Unmodified lignin | OLEA Value | OLEA Changes, % | OLEB Value | OLEB Changes, % | OLEC Value | OLEC Changes, % | OLED Value | OLED Changes, % |
|---|---|---|---|---|---|---|---|---|---|
| III, % (phenolic structure with C, OCH$_3$, OH) | 1.100 | 0.682 | −38.00 | 0.329 | −70.09 | 1.455 | 32.27 | 0.924 | −16.00 |
| IV, % (phenolic structure with C=, OCH$_3$, OH) | 0.054 | 0.019 | −64.81 | 0 | −100.00 | 0.099 | 83.33 | 0.041 | −24.07 |

Note:
The change percent was calculated as followed:
Change, % = (Value of bio-modified organosolv lignin samples-Value of organosolv lignin)/Value of organosolv lignin.
"—" means that the value of change is decreasing.

EXAMPLES 5-8

Modification of Ammonium Lignosulfonate with Different Fungi

The procedure and conditions were the same as EXAMPLES 1-4. The only difference was lignin type. Lignin used for EXAMPLES 5-8 was ammonium lignosulfonate. The example numbers and fungal species are listed in Table 3.

TABLE 3

Modification of ammonium lignosulfonate with different fungi

| EXAMPLE | Fungal specie | Type of fungi | Lignin | Code |
|---|---|---|---|---|
| 5 | *Pycnoporellus alboluteus* (Ellis & Everh.) Kotl. & Pouz. (FTK 76A) | brown-rot | Ammonium ligno-sulfonate (Tembec) | ALEA |
| 6 | *Phanerochaete cremea* (Bres.) Parmasto (FTK 332A) | white-rot | | ALEB |
| 7 | *Lenzites elegans* (Spreng.) Pat. (FTK 329A) | white-rot | | ALEC |
| 8 | *Meruliopsis taxicola* (Pers.) Bondartsev (FTK 122B) | brown-rot | | ALED |

EXAMPLES 9-12

Modification of Kraft Lignin with Different Fungi

The procedure and conditions were the same as EXAMPLES 1-4. The only difference was lignin type. Lignin used for EXAMPLES 9-12 was Kraft lignin. The example numbers and fungal species are listed in Table 4.

TABLE 4

Modification of Kraft lignin with different fungi

| EXAMPLE | Fungal specie | Type of fungi | Lignin | Code |
|---|---|---|---|---|
| 9 | *Pycnoporellus alboluteus* (Ellis & Everh.) Kotl. & Pouz. (FTK 76A) | brown-rot | Kraft lignin (Indulin AT) | KLEA |
| 10 | *Phanerochaete cremea* (Bres.) Parmasto (FTK 332A) | white-rot | | KLEB |
| 11 | *Lenzites elegans* (Spreng.) Pat. (FTK 329A) | white-rot | | KLEC |
| 12 | *Meruliopsis taxicola* (Pers.) Bondartsev (FTK 122B) | brown-rot | | KLED |

EXAMPLE 13

Synthesis of Fungal Modified Lignin (OLEA) Based Phenolic Resin for OSB Wood Composites 170 parts by weight of phenol (98%), 89 parts of fungal modified lignin (OLEA) from EXAMPLE 1 (moisture content of 6% wt), 146 parts by weight of paraformaldehyde (91% wt), 51 parts of sodium hydroxide (50 wt %), and 452 parts of water are needed.

In a 1-liter reaction kettle, phenol and OLEA were loaded, and ⅔ of the water amount to mix them. After around 10 minutes, paraformaldehyde was loaded, then part of sodium hydroxide (26 parts), and some more water to make the solid content in system around 50% (by weight). The mix was heated to around 70° C. for one and half an hour, then the remaining sodium hydroxide and all the remaining water were loaded, while maintaining temperature at around 70° C. for another half hour. After that, the temperature was increased to 80-90° C., until viscosity reached 150-200 cP. From practical experience, it is easier to control the synthesis of phenolic resin through lowering the temperature to 70-75° C. when the viscosity reaches 80-100 cP, then monitor the viscosity to the required level. The reaction was terminated by cooling down the system, with cold water, to around 30° C., and the resulted reactants were transferred to a container and stored in a cold room (4° C.) for further usage. The adhesive was coded OLEAPF.

EXAMPLES 14-16

Synthesis of Fungal Modified Lignin Based Phenolic Resin for OSB Wood Composites The lignin based phenolic resins are synthesized with different fungal modified lignin and different lignin substitutions of phenol. The synthesis procedure of lignin based phenolic resin is similar, the molar ratio of formaldehyde to phenol is the same, and ratio of sodium hydroxide to phenol and lignin are the same. The detail information is depicted in Table 5.

TABLE 5

Modified organosolv lignin based phenolic resins

| EXAMPLE | Code of lignin | Substitution phenol with lignin | Code of resin | NVC* (% wt) | Gel time** (sec) |
|---|---|---|---|---|---|
| 13 | OLEA from EXAMPLE 1 | 33 wt. % | OLEAPFA | 40.69 | 690 ± 11 |
| 14 | OLEA from EXAMPLE 1 | 50 wt. % | OLEAPFB | 41.70 | 877 ± 31 |
| 15 | OLEB from EXAMPLE 2 | 33 wt. % | OLEBPFA | 39.31 | 644 ± 16 |
| 16 | OLEB from EXAMPLE 2 | 50 wt. % | OLEBPFB | 39.66 | 756 ± 25 |
| Comparable Ex. 1 | Organosolv lignin without modification | 33 wt. % | OLPFA | 40.20 | 656 ± 19 |
| Comparable Ex. 2 | Organosolv lignin without modification | 50 wt. % | OLPFB | 40.94 | 792 ± 17 |

*NVC: non-volatile content;
**Gel time: 5 g/120° C.

COMPARABLE EXAMPLES 1-2

The similar lignin based phenolic resins are also synthesized with similar conditions in which organosolv lignin is not modified. The code and phenol replacement level are listed in Table 5.

EXAMPLE 17

Oriented Strand Board (OSB) Made with Modified Organosolv Lignin Based Phenolic Resin OSB panels are made with lignin-phenol-formaldehyde adhesives on face strands and a 100% commercial phenolic resin on core strands, under the pressing conditions listed in Table 6.

TABLE 6

OSB making conditions with phenolic resin

| | |
|---|---|
| Target panel density (OD basis) | 40 lbs/ft$^3$ |
| Mat dimensions | 20 in × 23 in |
| Target panel thickness | 11.1 mm (7/16 in) |
| Mat composition: face/core/face | 25/50/25 |
| Resin dosage Face: | 3% (solids on dry wood basis) |
| Core: | 3% (solids on dry wood basis) |
| Wax dosage | |
| Face: | 1% (solids on dry wood basis) |
| Core: | 1% (solids on dry wood basis) |
| Face wafer moisture before resin and wax | ~2% |
| Core wafer moisture before resin and wax | ~2.5% |
| Core moisture after resin and wax | ~3.5% |
| Face moisture after resin and wax | 7-8% |
| Press temperature (° C.) | 220° C. |
| Total press time | 150 seconds (daylight to daylight) |

TABLE 6-continued

OSB making conditions with phenolic resin

| | |
|---|---|
| Close time | 25 seconds |
| Degas | 25 seconds |

The mechanical properties of OSB panels, including thickness swelling (TS), water absorption (WA), internal bond (IB) strength, modulus of elasticity (MOE) and modulus of rupture (MOR) are measured according to ASTM D-1037 and all results are summarized in Table 7.

TABLE 7

Mechanical properties of OSB panels made with phenolic resins

| No. Example | Code | TS (%) | WA (% wt) | IB (MPa) | MOE (MPa) | MOR (MPa) |
|---|---|---|---|---|---|---|
| 13 | OLEAPFA | 20.52 ± 2.23 | 31.90 ± 1.79 | 0.41 ± 0.07 | 3711 ± 544 | 33.85 ± 3.30 |
| 14 | OLEAPFB | 18.17 ± 1.33 | 29.83 ± 1.73 | 0.46 ± 0.08 | 3510 ± 276 | 28.93 ± 6.23 |
| 15 | OLEBPFA | 19.12 ± 1.44 | 31.06 ± 1.74 | 0.43 ± 0.08 | 3854 ± 585 | 34.61 ± 6.60 |
| 16 | OLEBPFB | 29.84 ± 4.22 | 52.95 ± 2.96 | 0.48 ± 0.05 | 3651 ± 620 | 31.64 ± 4.53 |
| Comp. ex 1 | OLPFA | 31.58 ± 3.41 | 57.29 ± 4.78 | 0.46 ± 0.08 | 4054 ± 536 | 37.31 ± 5.13 |

TABLE 7-continued

Mechanical properties of OSB panels made with phenolic resins

| No. Example | Code | TS (%) | WA (% wt) | IB (MPa) | MOE (MPa) | MOR (MPa) |
|---|---|---|---|---|---|---|
| Comp. ex 2 | OLPFB | 32.01 ± 2.84 | 53.92 ± 7.24 | 0.35 ± 0.07 | 4124 ± 328 | 32.80 ± 5.13 |
| Com. PF | ComPF | 25.64 ± 0.86 | 45.17 ± 4.33 | 0.42 ± 0.08 | 3535 ± 419 | 27.44 ± 4.66 |

Comp. ex: comparable EXAMPLE;
Com. PF: commercial Phenolic resin

With 33% (w/w) phenol replacement, panels made with OLEAPFA (EXAMPLE 13) and OLEBPFA (EXAMPLE 15) had lower thickness swelling compared to the panels made with OLPFA (control). The water absorption of OSB panels made with OLEAPFA (EXAMPLE 13) and OLEBPFA (EXAMPLE 15) was lower than that with the panels made with OLPFA, even lower than that with the commercial phenolic face (ComPF) resin. The MOR, MOE and IB of panels made with OLEAPFA (EXAMPLE 13) and OLEBPFA (EXAMPLE 15) were comparable with those made with unmodified lignin based phenolic resin and commercial phenolic face resin.

With 50% (w/w) phenol replacement, panels made with OLEAPFB (EXAMPLE 14) had lower thickness swelling and water absorption compared to the panels made with and OLPFB, even lower than those made with the commercial phenolic face resin. The IB of panels made with OLEBPFB (EXAMPLE 16) was higher than that of panels made with OLPFB. The MOR and MOE were comparable with those made with unmodified lignin based phenolic resin OLPFB, and the commercial phenolic face resin.

With 50% (w/w) phenol replacement, panels made with OLEBPFB (EXAMPLE 16) had similar thickness swelling and water absorption compared to the panels made with OLPFB. The MOR, MOE and IB of panels made with OLEBPFB (EXAMPLE 16) were comparable with those made with unmodified lignin based phenolic resin OLPFB, and commercial phenolic face resin.

REFERENCES

Hüttermann, A., O. Milstein. B. Nicklas, J. Trojanowski, A. Haars, A. Kharazipour, *Lignin: Chapter 27: Enzymatic Modification of Lignin for Technical Use: Strategies and Results*, ACS Symposium Series, Vol. 397, pp 361-370 (1989)

Jin L, T. Sellers. Jr. T. P. Schultz and D. D. Nicholas. *Utilization of lignin modified by brown-rot fungi: I. Properties of Flakeboard Produced with a Brown-rotted Lignin Modified Phneolic Adhesive*, Holzforchung, 44, 207-210 (1990)

Li, K C, *From Mussels to decayed wood: an evolving story of developing green wood adhesives from renewable natural resources*, 39th International Wood Composites Symposium, APRIL 4-7, 2005, Pullman, Wash., USA Sellers, T. Jr., *Wood adhesive innovations and applications in North America*, Forest Products Journal, 51, 12-22 (2001)

Zakis, G. F. *Functional analysis of lignins and their derivatives*. TAPPI PRESS, 48-49 (1994)

The invention claimed is:
1. A process for the preparation of a phenol formaldehyde polymer resin comprising the steps of:
providing a fungal species selected from the group consisting of *Phanerochaete cremea* and *Pycnoporellus alboluteus* or combinations thereof;
providing a lignin;
mixing the fungal species and the lignin to produce a lignin/fungal species suspension;
incubating the suspension;
separating the suspension into a solid comprising the fungal species and a liquid comprising the lignin modified by the fungal species; and
treating the liquid to produce a reactive solid for the phenol formaldehyde polymer resin.
2. The process of claim 1, further comprising:
providing at least one phenolic compound, at least one formaldehyde compound, an alkali metal hydroxide and water;
mixing the at least one phenolic compound, the at least one formaldehyde compound, the alkali metal hydroxide, the water and the reactive solid to produce a methylolation medium;
maintaining the methylolation medium at a methylolation temperature to produce a methylolated medium with the formaldehyde compound reacting with the phenolic compound; and
increasing the temperature of the methylolated medium to produce the phenol-formaldehyde polymer resin via a condensation reaction.
3. The process of claim 2, further comprising adding more of the alkali metal hydroxide to the methylolated medium.
4. The process of claim 2, wherein the methylolation medium has a pH of about 10 or less.
5. A phenol formaldehyde adhesive polymer comprising:
a phenolic compound selected from the group consisting of phenol, a lignin and combinations thereof;
a formaldehyde compound selected from the group consisting of formaldehyde, paraformaldehyde and combinations thereof;
water; and
an alkali metal hydroxide;
wherein the lignin is a modified lignin that is modified by *Phanerochaete cremea*, *Pycnoporellus alboluteus*, or combinations thereof,
wherein the phenolic compound comprises at least 33% by weight of the modified lignin .
6. The polymer of claim 5, wherein the phenolic compound comprises 50% by weight of the modified lignin.
7. A plywood or an oriented strand board comprising phenol formaldehyde adhesive polymer between wooden layers of the plywood or oriented strand board; wherein the adhesive polymer comprising:
a phenolic compound selected from the group consisting of phenol, a lignin and combinations thereof;
a formaldehyde compound selected from the group consisting of formaldehyde, paraformaldehyde and combinations thereof;
water; and
an alkali metal hydroxide;
wherein the lignin is a modified lignin that is modified by *Phanerochaete cremea*, *Pycnoporellus alboluteus*, or combinations thereof, wherein the phenolic compound comprises at least 3% by weigh of the modified lignin.

8. The plywood or oriented strand board of claim 7, wherein the phenolic compound comprises at least 50% by weight of the modified lignin.

* * * * *